(12) United States Patent
Ahn et al.

(10) Patent No.: US 8,426,900 B2
(45) Date of Patent: Apr. 23, 2013

(54) SENSING DEVICE

(75) Inventors: Chang Geun Ahn, Daejeon (KR); Chan Woo Park, Daejeon (KR); Jong Heon Yang, Daejeon (KR); In Bok Baek, Cheongju-si (KR); Chil Seong Ah, Daejeon (KR); An Soon Kim, Daejeon (KR); Tae Youb Kim, Seoul (KR); Gun Yong Sung, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 209 days.

(21) Appl. No.: 13/122,273

(22) PCT Filed: May 27, 2009

(86) PCT No.: PCT/KR2009/002796
§ 371 (c)(1),
(2), (4) Date: Apr. 1, 2011

(87) PCT Pub. No.: WO2010/041805
PCT Pub. Date: Apr. 15, 2010

(65) Prior Publication Data
US 2011/0180856 A1 Jul. 28, 2011

(30) Foreign Application Priority Data
Oct. 7, 2008 (KR) .................. 10-2008-0098141

(51) Int. Cl.
*G01N 27/403* (2006.01)
(52) U.S. Cl.
USPC .... 257/253; 257/277; 257/296; 257/E29.255; 977/762; 977/920
(58) Field of Classification Search ............. 257/253, 257/277, 296, E29.255; 977/762, 920
See application file for complete search history.

(56) References Cited

U.S. PATENT DOCUMENTS

| 7,947,485 | B2* | 5/2011 | Wu et al. ............... 435/283.1 |
| 2002/0006632 | A1 | 1/2002 | Ponnampalam et al. |
| 2005/0053524 | A1 | 3/2005 | Keersmaecker et al. |
| 2005/0263410 | A1 | 12/2005 | Hsiung |

(Continued)

FOREIGN PATENT DOCUMENTS

| DE | 10221799 A1 | 11/2003 |
| JP | 2003-322633 | 11/2003 |

(Continued)

OTHER PUBLICATIONS

Barbaro, Massimo et al., "Fully electronic DNA hybridization detection by a standard CMOS biochip," Sensors and Actuators B, vol. 118:41-46 (2006).

(Continued)

*Primary Examiner* — Tu-Tu Ho
(74) *Attorney, Agent, or Firm* — Nelson Mullins Riley & Scarborough LLP; EuiHoon Lee, Esq.

(57) ABSTRACT

Provided is a sensing device, which includes a reactive material layer (260) responding to a specific functional group in a fluid, a sensing capacitor (B) including first and second electrodes disposed on and under an insulating layer (230), the first electrode being disposed under the reactive material layer (260), and a field effect transistor including a gate electrode connected with the first electrode of the sensing capacitor. Here, the reactive material layer (260) is formed in a conductive three-dimensional structure to widen a surface area. Thus, the sensing device may have high sensitivity by maximizing a capacitor sharing effect and a change in voltage amount applied to a gate, which may be caused by widening a surface area of the conductive three-dimensional structure with respect to the fluid flow.

12 Claims, 4 Drawing Sheets

U.S. PATENT DOCUMENTS

2007/0207471 A1    9/2007    Osaka et al.

FOREIGN PATENT DOCUMENTS

| | | |
|---|---|---|
| JP | 2007-139762 | 6/2007 |
| JP | 2008-134255 | 6/2008 |
| WO | 2007/084077 A1 | 7/2007 |

OTHER PUBLICATIONS

Cohen, Ariel et al., "Depletion type floating gate p-channel MOS transistor for recording action potentials generated by cultured neurons," Biosensors and Bioelectronics, vol. 19:1703-1709 (2004).

* cited by examiner (a)

(b)

(c)

SENSING DEVICE

RELATED APPLICATIONS

This application is a 35 U.S.C. §371 national stage filing of PCT Application No. PCT/KR2009/002796 filed on May 27, 2009, which claims priority to, and the benefit of, Korean Patent Application No. 10-2008-0098141 filed Oct. 7, 2008. The contents of the aforementioned applications are hereby incorporated by reference.

TECHNICAL FIELD

The present invention relates to a sensing device for sensing a specific functional group present in a fluid, and more particularly, to a biosensor for sensing a bio-molecule having a specific functional group.

BACKGROUND ART

It is expected that a sensing device for sensing a specific functional group present in a fluid will be widely applied in the field of biosensors sensing the presence or absence of an amino acid or a DNA molecule in a body fluid.

Recently, there has been a rapid movement to develop a new technological base by converging Information Technology (IT) and Nano Technology (NT), which have heretofore been independently developing, with Biotechnology (BT). Particularly, in a nano-biochip field that is one of nano-bio (NT-BT) convergence technology, a biosensor for sensing protein in a blood is actively studied.

In the nano-biochip field, various methods for sensing, analyzing and quantifying a specific bio material are developing. Among these methods, a method of sensing a specific bio-material by fluorescence labeling is typical. This method is widely applied in currently-available DNA chips.

However, the fluorescence labeling method is difficult to apply to various materials because it requires an additional bio-chemical preparation step of a test sample such as blood or saliva in order to sense a specific bio-material.

For example, in the case of protein labeling, about 50% of functional protein is in-activated during an unspecific labeling process. Accordingly, only a very small amount of analyte is available for the purpose.

For this reason, biosensors based on silicon, which improve sensitivity or reproducibility and are capable of being mass-produced using a semiconductor process, have been introduced.

For example, a biosensor having high-sensitivity and capable of sensing a specific material using a silicon nano wire (Si-nano wire) formed by a CVD growth technique in a bottom-up approach has been widely studied in recent years, however a study on a Si-nano wire biosensor capable of being mass-produced using an industrial CMOS manufacturing process, which is easily implemented and ensures reproducibility in a top-down approach is more actively progressing.

In addition, many study results on an ion-sensitive field effect transistor (ISFET) having a field effect transistor (FET)-type device and also using a CMOS process have been disclosed.

The ISFET is similar to a nano wire biosensor in an aspect of changing conductivity of the sensor by increasing a surface charge by interaction between a target molecule in a solution and a probe molecule of a sensor. However, it is characterized in an aspect of having a common field effect transistor structure and determining a gate voltage according to a target molecule adsorbed to a top of a gate, the gate voltage corresponding to a pattern of an operating characteristic curve of a transistor.

However, it is difficult to make a wide variation of the total gate voltage due to a variation in amount of charge generated by interaction between the probe molecule and the target molecule, and thus sensitivity of the device is significantly decreased.

DISCLOSURE OF INVENTION

Technical Problem

The present invention is directed to a sensing device having improved sensing ability.

Technical Solution

One aspect of the present invention provides a sensing device, including: a reactive material layer responding to a specific functional group in a fluid; a sensing capacitor including first and second electrodes disposed on and under an insulating layer, the first electrode being formed under the reactive material layer; and a field effect transistor including a gate electrode connected with the first electrode of the sensing capacitor. Here, the reactive material layer has a conductive three-dimensional structure to widen a surface area.

The second electrode may be conductively connected with a source electrode of the field effect transistor, and formed of a material having a higher conductivity than a substrate of the field effect transistor.

The first electrode may be formed of the same material as the gate electrode.

An insulating layer of the sensing capacitor may be thicker than a gate insulating layer of the field effect transistor.

A capacitance of the sensing capacitor may be smaller than ⅕ of a gate capacitance of the field effect transistor.

The field effect transistor may include source and drain electrodes through which a current flows by a variation in amount of charge of the gate electrode, a gate insulating layer formed to cover the source and drain electrodes and a channel, and the gate electrode formed on the gate insulating layer and connected with one electrode of the sensing capacitor.

The conductive three-dimensional structure may be mesh, column, or piled-up nanoparticle shape.

The conductive three-dimensional structure may be formed by a mesh-shaped metal nano wire structure.

The insulating layer of the sensing capacitor may be formed in a sheet shape to deliver a fluid to be sensed, the first electrode may have a sheet shape in contact with a top of the insulating layer, the second electrode may have a sheet shape in contact with a bottom of the insulating layer, and the conductive three-dimensional structure may be disposed on the first electrode.

The insulating layer of the sensing capacitor may be formed of a dielectric layer, as an example polymer synthetic resin or glass, and the first and second electrodes may be formed of a metal.

The insulating layer of the sensing capacitor may have a pipe shape to deliver a fluid to be sensed, the first electrode may have a pipe shape in contact with the inside of the insulating layer, the second electrode may be a pipe shape in contact with the outside of the insulating layer, and the conductive three-dimensional structure may be disposed inside the first electrode.

An insulating layer of the sensing capacitor may be formed of polymer synthetic resin, and the first and second electrodes may be formed of a metal.

Advantageous Effects

According to the present invention, a sensing device uses an electrical characteristic in a sub-threshold range of a transistor and is formed to have a large surface area of a conductive three-dimensional structure of a charge accumulation part and a three-dimensional structure with respect to the flow of a fluid. Thus, the sensing device enables maximization of a capacitor sharing effect and a voltage variation supplied to a gate, thereby obtaining very high sensitivity.

In addition, the sensing device of the present invention has a pipe-shaped capacitor, which facilitates the sensing device to be manufactured in simple process and configuration, ensures durability of the sensing device, and is easily applied and replaced.

BRIEF DESCRIPTION OF DRAWINGS

The above and other objects, features and advantages of the present invention will become more apparent to those of ordinary skill in the art by describing in detail exemplary embodiments thereof with reference to the accompanying drawings, in which.

MODE FOR THE INVENTION

Figure 1:
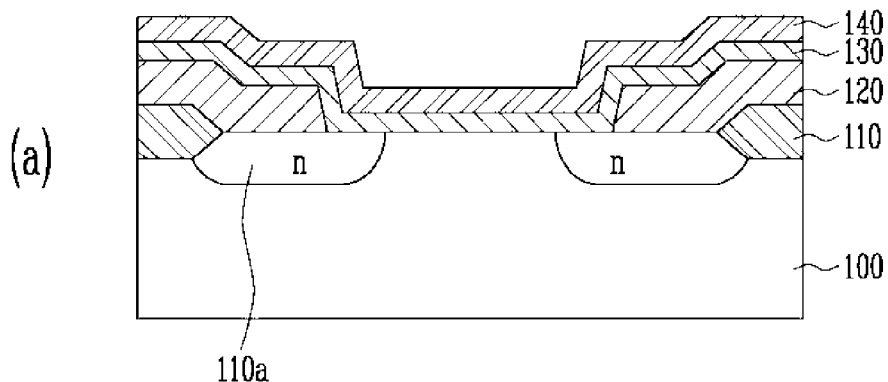
FIGS. 1A to 1C are views for explaining an operating principle of an ion-sensitive field effect transistor.
Figure 1:
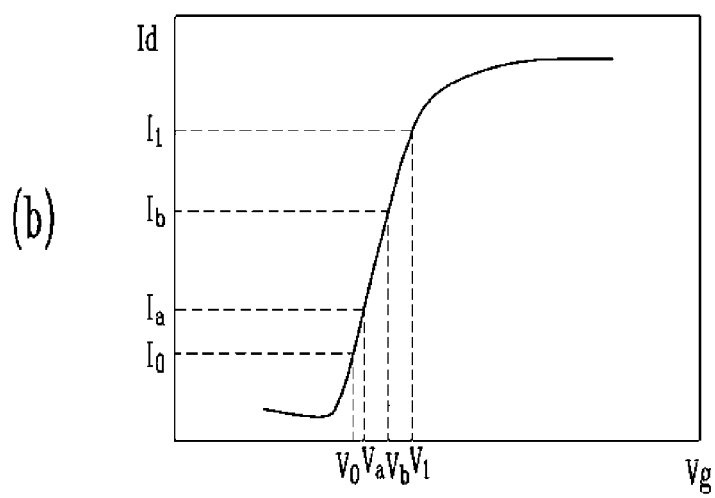
Figure 1:
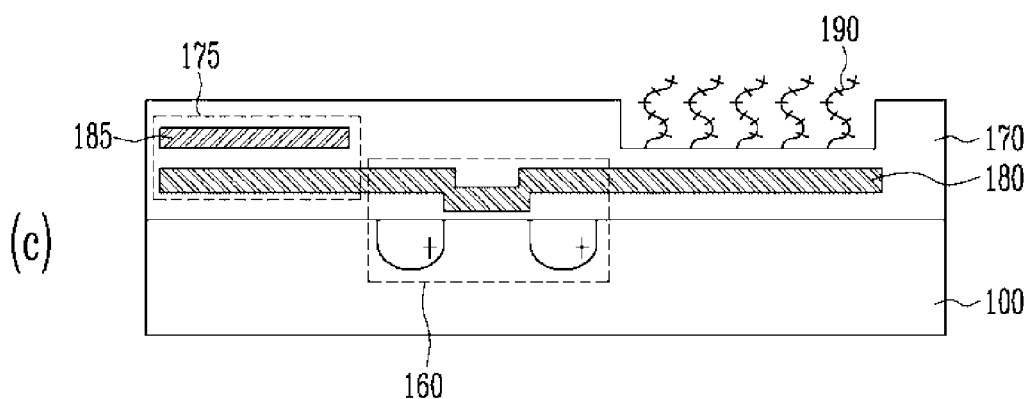

Hereinafter, exemplary embodiments of the present invention will be described in detail. However, the present invention is not limited to the exemplary embodiments disclosed below, but can be implemented in various modified forms. For clarity of descriptions, elements in the drawings, which do not relate thereto, will be omitted, and like reference numerals denote like elements throughout the specification.

Throughout the specification, when one part is "connected" with another part, it may be "directly connected," or "electrically connected" with another part to have a third part interposed therebetween.

In addition, when one part "includes" one element, it should be understood that the present invention is not limited to the number of the element, and thus may further include another element, except as specifically described.

Now, technology of manufacturing a biosensor having a sensitive structure to sense a specific bio-material by separately forming a charge accumulation part capable of storing charges in an ion-sensitive field effect transistor, and delivering the storing charges to a gate to maximize the variation in amount of charge generated by an interaction between a probe molecule and a target molecule will be described.

FIGS. 1A and 1B are views for explaining an operating principle of an ion-sensitive field effect transistor.

Referring to FIG. 1A, an ion-sensitive field effect transistor having source and drain electrodes 120 and a plurality of insulating layers 110, 130 and 140 formed on a substrate 100 having source and drain regions 110a is formed in a common configuration, but it does not have a gate electrode controlling a channel.

When a probe molecule (not shown) responding to a specific functional group in a body fluid is fixed on the channel, the probe molecule reacts with a target molecule having the specific functional group, a control power of the gate electrode is changed by a variation in amount of charge of the target molecule, and a current between the source and drain electrodes 120 is changed.

Referring to an electrical characteristic curve of a drain current according to a gate voltage of the field effect transistor shown in FIG. 1B, the drain current is very sensitive to the gate voltage in a sub-threshold range ($V_0$ to $V_1$).

When the drain current is Ia at an initial gate voltage of Va, a target molecule binds to a probe molecule placed on a gate surface so as to induce a change in gate voltage. Accordingly, the gate voltage is changed to Vb, and the drain current becomes Ib.

Accordingly, when such a sub-threshold range is used as a sensing range, a subtle change in gate voltage may induce a great change in drain current that is a sensing signal.

However, at present, the gate voltage variation induced in response to a surface reaction per unit area is too small to obtain large variation in drain current that is the sensing signal. Therefore, the sensitivity of the sensor is not high enough.

FIG. 1C is a schematic cross-sectional view of an ion-sensitive field effect transistor of a sensing device having a control electrode part.

Unlike FIG. 1A, a sensing device includes a control electrode part 175 having a control electrode 185 and generating a standard voltage on an insulating layer 170 of a transistor 160, and a separate charge accumulation part 180, which has a large area, without exposing a top of a channel. That is, the charge accumulation part 180 having a large area, instead of using the narrow top of the channel, is formed and a charge variation is sensed from reactive material 190, and thus the sensing device may obtain consistent results.

However, as the charge accumulation part 180 becomes larger in order to increase the accumulated charge amount, a capacitance is also increased by the same amount as the increased area, and thus a variation in gate voltage is uniform regardless of the change in area.

A sensing device capable of increasing the variation in gate voltage will be described below.

Figure 2:
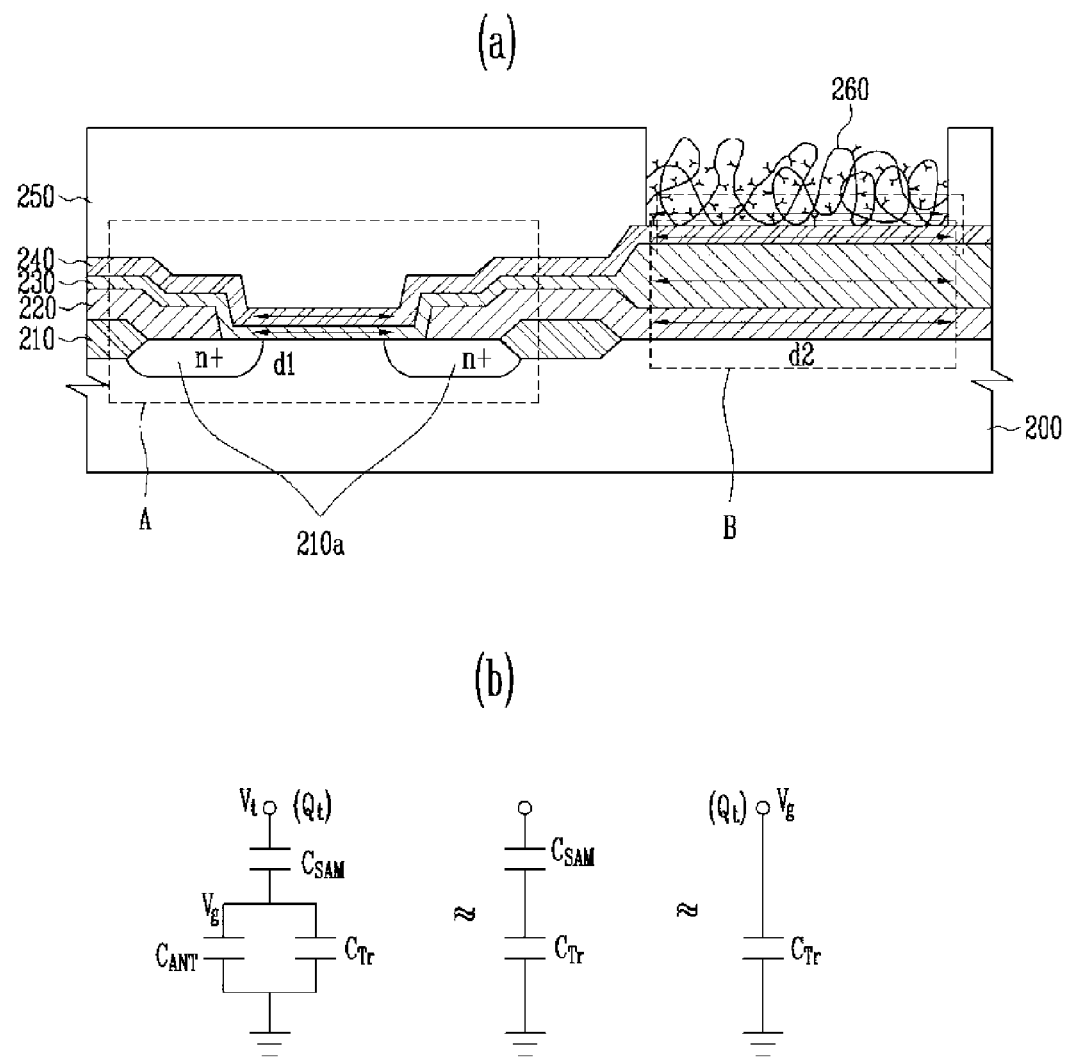
FIG. 2A is a cross-sectional view of a sensing device according to an exemplary embodiment of the present invention.
FIG. 2B is an equivalent circuit diagram for explaining an operating principle of a biosensor of FIG. 2A.

FIG. 2A is a cross-sectional view of a sensing device according to an exemplary embodiment of the present invention, and FIG. 2B is an equivalent circuit diagram for explaining an operating principle of a biosensor of FIG. 2A.

The sensing device of the present invention is formed of a field effect transistor A and a sensing capacitor B.

The field effect transistor A includes an isolation layer 210, source and drain electrodes 220 through which a current flows according to a change in amount of charge of a gate electrode 240, a gate insulating layer 230 formed to cover the source and drain electrodes 220 and the channel, and the gate electrode 240 which are formed on a substrate 200 formed of, for example, polysilicon and including a channel having a width d1 and source and drain regions 210a.

Here, the gate insulating layer 230 and the gate electrode 240 extend to the sensing capacitor region B, and the gate electrode 240 is connected with a first electrode of the sensing capacitor B. In order to improve another specific characteristic, the gate electrode 240 may be implemented to be separate from the first electrode of the sensing capacitor B using separate process and material.

An insulating layer 250, which is a passivation layer, is formed on the gate electrode 240.

The sensing capacitor B includes the first electrode connected with the gate electrode 240, an insulating layer formed under the first electrode, and a second electrode.

The insulating layer of the sensing capacitor B may be formed of a silicon oxide layer, which is the same as the gate insulating layer 230. Here, the insulating layer of the sensing capacitor B may be formed significantly thicker than the gate insulating layer 230, thereby reducing capacitance of the sensing capacitor B. Such a very thick insulating layer makes a great change in operating characteristic of the device.

Here, the gate insulating layer 230 and the insulating layer of the sensing capacitor B may be formed in one process, or may be formed in different processes. For example, while the gate insulating layer 230 may be formed of silicon oxide or a high-k material, the insulating layer of the capacitor B may be formed of a low-k material to obtain a sufficiently small capacitance even with a small thickness.

In the sensing capacitor B, the first electrode covered with the insulating layer 250 is partially exposed, and a reactive material layer 260 having a probe molecule responding to a specific functional group in a fluid is further included on the exposed first electrode.

The reactive material layer 260 may have a three-dimensional structure to increase a probability of the reaction to a reactive material to be sensed, for example, a metal nano-wire structure having a mesh shape like a cotton ball, a mesh structure having a sheet shape, a column-shaped structure or piled-up nanoparticle structure.

The reactive material layer 260 having such a conductive three-dimensional structure must be in electrical contact with the first electrode.

In addition, the first and second electrodes of the sensing capacitor B may be implemented of another conductive material having a higher conductivity than the substrate 200, which is a p-type substrate, of the transistor A.

The second electrode of the sensing capacitor B, which is a polysilicon layer, may be omitted, but if it is present, performance of delivering a changed characteristic of the sensing capacitor due to the specific functional group contained in a specimen fluid to a source of the field effect transistor is improved.

When no electrode is present between the substrate 200 and the insulating layer of the sensing capacitor B, the substrate 200 serves as a second electrode of the capacitor. In this case, the second electrode of the sensing capacitor B and the substrate 200 of the field effect transistor A are shared, which may reduce flexibility of controlling a bias between the sensing capacitor B and the field effect transistor A, and thus an additional process for grounding the substrate 200 is required. Also, a bias may be applied at the interface between the substrate 200 and the insulating layer of the sensing capacitor B because of the characteristic thereof. Such a bias may generally cause depletion around the second electrode of the substrate since the second electrode is formed of bulk silicon doped at a low concentration, so that the capacitance may be changed unnecessarily. For this reason, the second electrode of the sensing capacitor B may be formed of a material having a higher conductivity than the substrate 200 (e.g., metal or polysilicon), which is a p-type substrate, of the field effect transistor A in a different process from that for the substrate.

The structure shown in FIG. 2A may be expressed as an electrical equivalent circuit on the left side of FIG. 2B.

Here, when the sensing capacitor B that is the charge accumulation part becomes larger, $C_{ANT}$ is increased, but when the insulating layer of the sensing capacitor B becomes thicker, $C_{ANT}$ is decreased. Using such characteristics, if a value of $C_{ANT}$ is given to be much lower, e.g., at least 5 times lower than that of $C_{Tr}$, the result can be simply expressed as an equivalent circuit in the middle. That is, when the thickness of the insulating layer is increased as much as an increased area of the active layer of the sensing capacitor B, and preferably, is controlled to be 5 times lower than that of $C_{Tr}$, an influence of $C_{ANT}$ may be reduced as much as possible.

$C_{ANT}$ and $C_{Tr}$ are determined by an area ($A_{ANT}$) of the sensing capacitor B, an area ($A_{gate}$) of a channel of the transistor A, thickness ($t_{ANT}$) and permittivity ($\epsilon_{ANT}$) of the insulating layer of the capacitor, and thickness ($t_{OX}$) and permittivity ($\epsilon_{OX}$) of the gate insulating layer 230. Thus, these parameters should satisfy the relationship of the following mathematical formula. This is because if a capacitance difference is about 5 times, the influence of one party can be ignored.

[Formula 1]

$$5C_{ANT} \leq C_{Tr} \Leftrightarrow 5\epsilon_{ANT} A_{ANT}/t_{ANT} \leq \epsilon_{OX} A_{gate}/t_{OX}$$

Moreover, when a surface area of an upper electrode of the sensing capacitor B is much larger than the gate area of the transistor A, and the height of a linked material layer forming $C_{SAM}$ is generally much smaller than the gate insulating layer 230, the equivalent circuit in the middle may be simply changed into an equivalent circuit on the right side. It can be noted from the equivalent circuit on the right side that since the total equivalent capacitance is uniform as the capacitance of the transistor $C_{Tr}$, as more reactions of the target material are induced through the large charge accumulation part, the device can obtain a wide variation in amount of charge and a wide variation in gate voltage at the same time.

According to the implementation of the sensing device of the present exemplary embodiment, a plurality of sensing capacitors B may be included, or a plurality of structures including the sensing capacitor B and the field effect transistor A shown in FIG. 2A may be included. In this case, a reactive material layer 260 having a different probe molecule fixed on a surface of each capacitor B may be formed.

Meanwhile, the probe molecule constituting the reactive material layer 260 of the present exemplary embodiment may be formed of any one selected from the group consisting of an antigen, an antibody, DNA, protein and a combination thereof.

Figure 3:
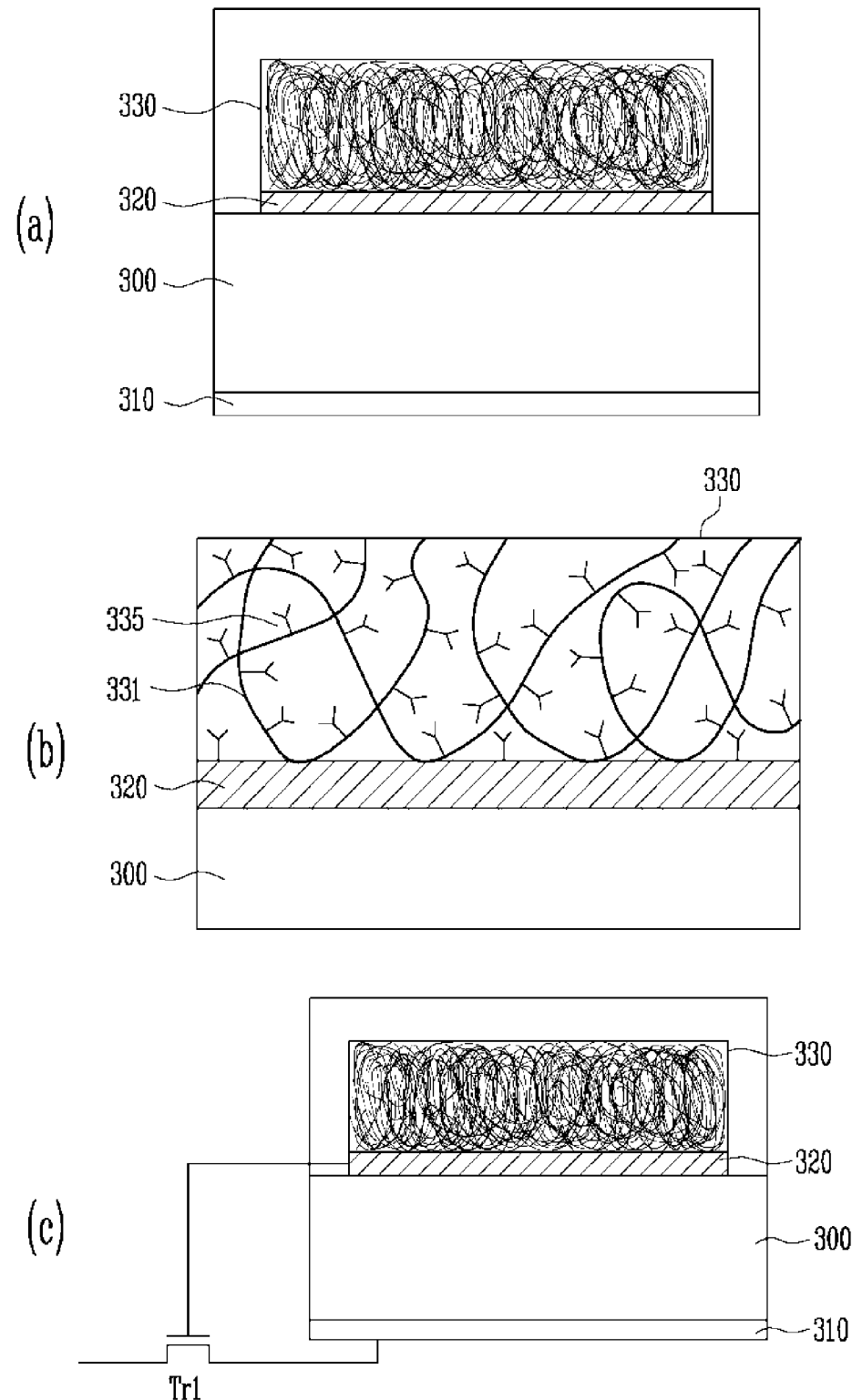
FIGS. 3A to 3C are views of a sensing device having a sensing capacitor formed using a different substrate, instead of a silicon substrate.

Another exemplary embodiment of the present invention will be described with reference to FIGS. 3A to 3C below.

FIGS. 3A to 3C show a structure of a sensing device having a sensing capacitor formed using a different substrate, not a silicon substrate.

Like the sensing device shown in FIG. 2A, a sensing device includes a field effect transistor and a sensing capacitor for storing charges.

The field effect transistor of the shown sensing device may have a cheap and reproducible structure since a commonly available and complete-packaging transistor is placed in a reader, and a part of a pipe where a specimen fluid flows may be implemented as a sensing capacitor.

That is, a sheet-shaped sensing capacitor of the exemplary embodiment has an insulating substrate 300 formed of an insulating or dielectric material as an insulating layer of the sensing capacitor, and also has conductive substrates 310 and 320 on and under the insulating substrate, respectively, to serve as two electrodes.

A reactive material layer 330 having a conductive three-dimensional structure is formed on a first electrode.

The conductive substrates 310 and 320 may be formed of a metal, and the insulating substrate 300 may be formed of polymer synthetic resin or glass.

The upper conductive substrate 320 corresponding to the first electrode may be coated with a specific material facilitating surface immobilization treatment with respect to a probe molecule 335 constituting the reactive material layer 330, for example, gold (Au), or formed of a material itself capable of surface immobilizing the probe molecule. Thus, in the present exemplary embodiment, the probe molecule 335 responding to a specific functional group in a specimen fluid may be in direct contact with the upper conductive substrate 320, in contact with the material layer capable of surface immobilization, which is coated on the upper conductive substrate 320, or placed at a conductive three-dimensional structure 331 on the upper conductive substrate 320 constituting the reactive material layer 330.

In the exemplary embodiment, the insulating substrate 300 is present between the upper conductive substrate 320 and the lower conductive substrate 310, and thus a capacitor structure is completed. Here, sizes of both substrates may be different from each other in order to control sensitivity and an analyzable region. Also, the upper and lower conductive substrates 310 and 320 may be designed not to be conductively connected with each other, and to facilitate a contact with an external electrode.

Figure 4:
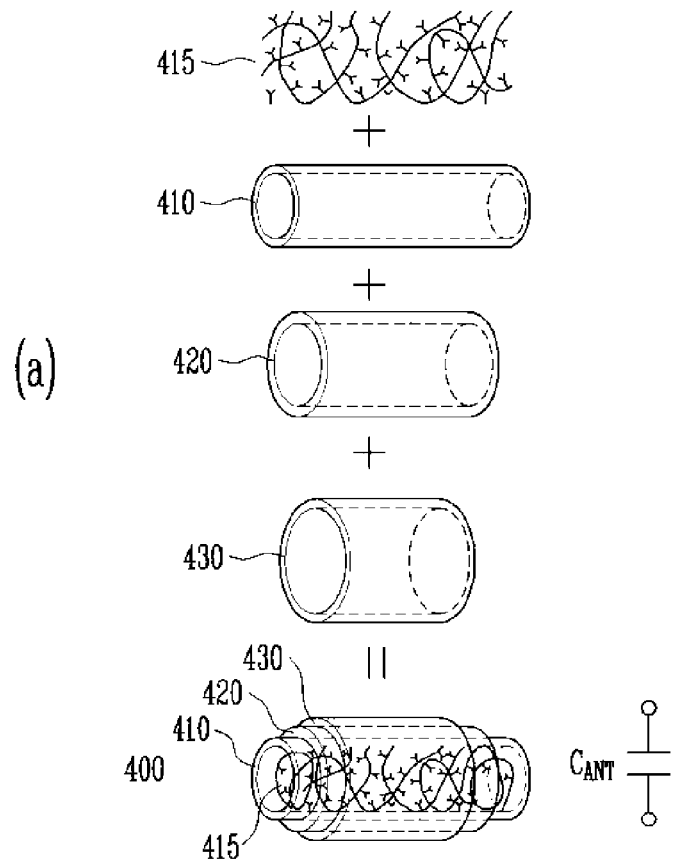
FIGS. 4A to 4C are views of a pipe-type sensing capacitor.
Figure 4:
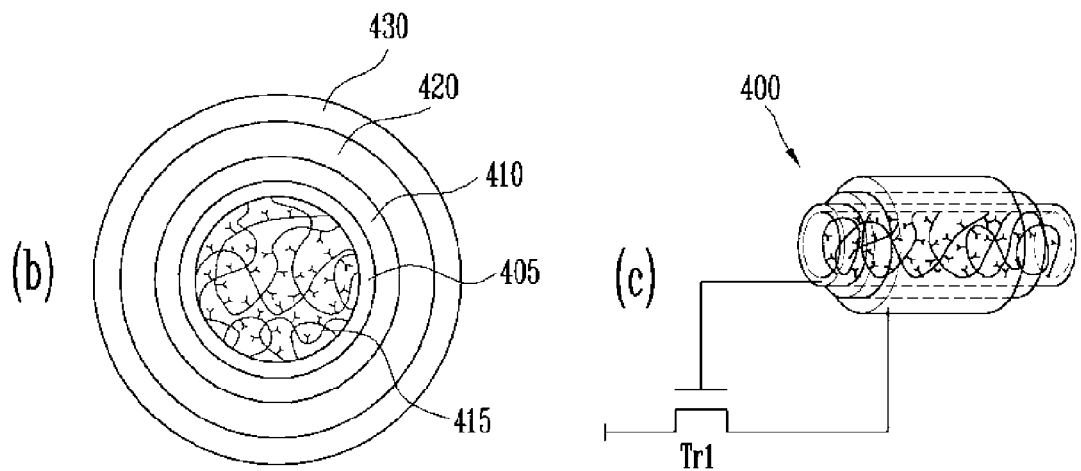

Next, another exemplary embodiment of the present invention will be described with reference to FIGS. 4A to 4C.

FIGS. 4A to 4C show a sensing capacitor implemented in a pipe shape, in which an insulating pipe 420 formed of an insulating or dielectric material serves as an insulating layer material of the capacitor, and two other conductive pipes 410 and 430 joined to inner and outer surfaces of the pipe serve as first and second electrodes of the capacitor. The conductive pipes 410 and 430 may be easily formed of a metal pipe. The insulating pipe 420 may be formed of polymer synthetic resin.

The inner conductive pipe 410 corresponding to the first electrode may be coated with a specific material facilitating surface immobilization treatment with respect to a probe molecule constituting a reactive material layer 415, for example, gold (Au), or formed of a material itself capable of surface-fixing the probe molecule. Thus, in the present exemplary embodiment, the probe molecule of the reactive material layer 415 responding to a specific functional group in a specimen fluid may be in direct contact with the inner conductive pipe 410, in contact with the material layer capable of surface immobilization, which is coated on an inside of the inner conductive pipe 410, or placed at a conductive three-dimensional structure in the inner conductive pipe 410.

In the present exemplary embodiment, the insulating pipe 420 is present between the inner conductive pipe 410 and the outer conductive pipe 430, and thus a capacitor structure is completed. Here, sizes, diameters or shapes of the pipes may be changed in order to control sensitivity and an analyzable region. Also, the inner and outer conductive pipes 410 and 430 may be designed not to be in conductively connected with each other, but to facilitate a contact with an external electrode.

The sensing procedures of the sensing devices shown in FIGS. 2A to 4C will be described below. As described above, the sensing of the target molecule including a specific functional group in response to a reaction of a probe molecule in the reactive material layer causes a variation in charge amount of the sensing capacitor, and a variation in gate voltage of the field effect transistor in which a gate and a source are respectively connected to both electrodes of the sensing capacitor. These variations caused by reacting the target molecule and the probe molecule are read by a reader in the form of a drain current variation, and the read data may be displayed as sensing results by various known analyses.

To sense the target molecule, the transistor should use an electronic characteristic in a sub-threshold range that is sensitive to a current change according to a voltage change in the field effect transistor, and the gate voltage change in response to the reaction of the reactive material layer should be controlled by adjusting specifications of the sensing capacitor and the field effect transistor and an external bias in order to be applied in the sub-threshold range of the field effect transistor.

Other than when a source and a drain are specifically formed to have asymmetrical characteristics, distinction of a source from a drain in a common MOS transistor is relative. Thus, it should be understood that the source and the drain are distinguished only for convenience of the descriptions, and thus the present invention is not limited to such distinction.

Exemplary embodiments of the present invention are not to be implemented only by the devices and methods described above, but may be implemented by a program realizing a function corresponding to the configurations of the exemplary embodiments of the present invention or by a recording medium in which the program is recorded. Such implementations may be easily obtained by those skilled in the art from the descriptions of the above exemplary embodiment.

While the invention has been shown and described with reference to certain exemplary embodiments thereof, it will be understood by those skilled in the art that various changes in form and details may be made therein without departing from the spirit and scope of the invention as defined by the appended claims.

The invention claimed is:

1. A sensing device, comprising:
a reactive material layer responding to a specific functional group in a fluid;
a sensing capacitor including first and second electrodes disposed on and under an insulating layer, the first electrode being formed under the reactive material layer; and
a field effect transistor including a gate electrode connected with the first electrode of the sensing capacitor,
wherein the reactive material layer has a conductive three-dimensional structure to widen a surface area.

2. The sensing device according to claim 1, wherein the second electrode is conductively connected with a source electrode of the field effect transistor, and formed of material having a higher conductivity than a substrate of the field effect transistor.

3. The sensing device according to claim 2, wherein the first electrode is formed of the same material as the gate electrode.

4. The sensing device according to claim 1, wherein an insulating layer of the sensing capacitor is thicker than a gate insulating layer of the field effect transistor.

5. The sensing device according to claim 4, wherein a capacitance of the sensing capacitor is smaller than $1/5$ of a gate capacitance of the field effect transistor.

6. The sensing device according to claim 1, wherein the field effect transistor includes source and drain electrodes through which a current flows by a variation in amount of charge of the gate electrode, a gate insulating layer formed to cover the source and drain electrodes and a channel, and the gate electrode formed on the gate insulating layer and connected with one electrode of the sensing capacitor.

7. The sensing device according to claim 1, wherein the conductive three-dimensional structure is a mesh or column shape.

8. The sensing device according to claim 7, wherein the conductive three-dimensional structure is constructed by a mesh-shaped metal nano wire structure.

9. The sensing device according to claim 1, wherein the insulating layer of the sensing capacitor has a sheet shape to deliver a fluid to be sensed inside, the first electrode has a sheet shape in contact with a top of the insulating layer, the second electrode has a sheet shape in contact with a bottom of the insulating layer, and the conductive three-dimensional structure is disposed on the first electrode.

10. The sensing device according to claim 9, wherein the insulating layer of the sensing capacitor is formed of polymer synthetic resin or glass, and the first and second electrodes are formed of a metal.

11. The sensing device according to claim 1, wherein the insulating layer of the sensing capacitor has a pipe shape to deliver a fluid to be sensed inside, the first electrode has a pipe shape in contact with the inside of the insulating layer, the second electrode is a pipe shape in contact with the outside of the insulating layer, and the conductive three-dimensional structure is disposed inside the first electrode.

12. The sensing device according to claim 11, wherein the insulating layer of the sensing capacitor is formed of polymer synthetic resin, and the first and second electrodes are formed of a metal.

\* \* \* \* \*